United States Patent
Dorn et al.

(10) Patent No.: US 8,712,799 B2
(45) Date of Patent: Apr. 29, 2014

(54) METHOD OF PROVIDING TAILOR-MADE SOFTWARE FOR HOSPITAL DEPARTMENTS

(75) Inventors: Karlheinz Dorn, Kalchreuth (DE); Andrew John Hewett, Erlangen (DE); Vladyslav Ukis, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 372 days.

(21) Appl. No.: 12/320,039

(22) Filed: Jan. 15, 2009

(65) Prior Publication Data

US 2010/0179826 A1     Jul. 15, 2010

(51) Int. Cl.
*G06F 19/00*     (2011.01)
(52) U.S. Cl.
USPC .................................. 705/3; 705/2; 709/202
(58) Field of Classification Search
USPC .................................. 705/2, 3; 709/202; 1/1
See application file for complete search history.

(56) References Cited

U.S. PATENT DOCUMENTS

| | | | |
|---|---|---|---|
| 5,471,615 A * | 11/1995 | Amatsu et al. | 709/202 |
| 6,556,999 B1 * | 4/2003 | Kloos et al. | 1/1 |
| 7,089,247 B2 * | 8/2006 | Kloos et al. | 1/1 |
| 2010/0017231 A1 * | 1/2010 | Galbraith et al. | 705/3 |
| 2010/0138231 A1 * | 6/2010 | Linthicum et al. | 705/2 |

OTHER PUBLICATIONS

Google search, Dec. 2, 2013.*

* cited by examiner

*Primary Examiner* — Dilek B Cobanoglu
(74) *Attorney, Agent, or Firm* — Harness, Dickey & Pierce, P.L.C.

(57) ABSTRACT

To provide tailor-made software for use in a specific department of a hospital, a software package suitable for use by more than one department of the hospital is provided including components implementing general tasks. Then, software is added implementing tasks which may be considered to extend the general tasks. This extension can be tailor-made for the specific department. In at least one embodiment, the software package includes both front end and back end software components, front end components reacting to user inputs and calling up back end software components, and the extension may be both at the front end and at the back end side.

9 Claims, 1 Drawing Sheet

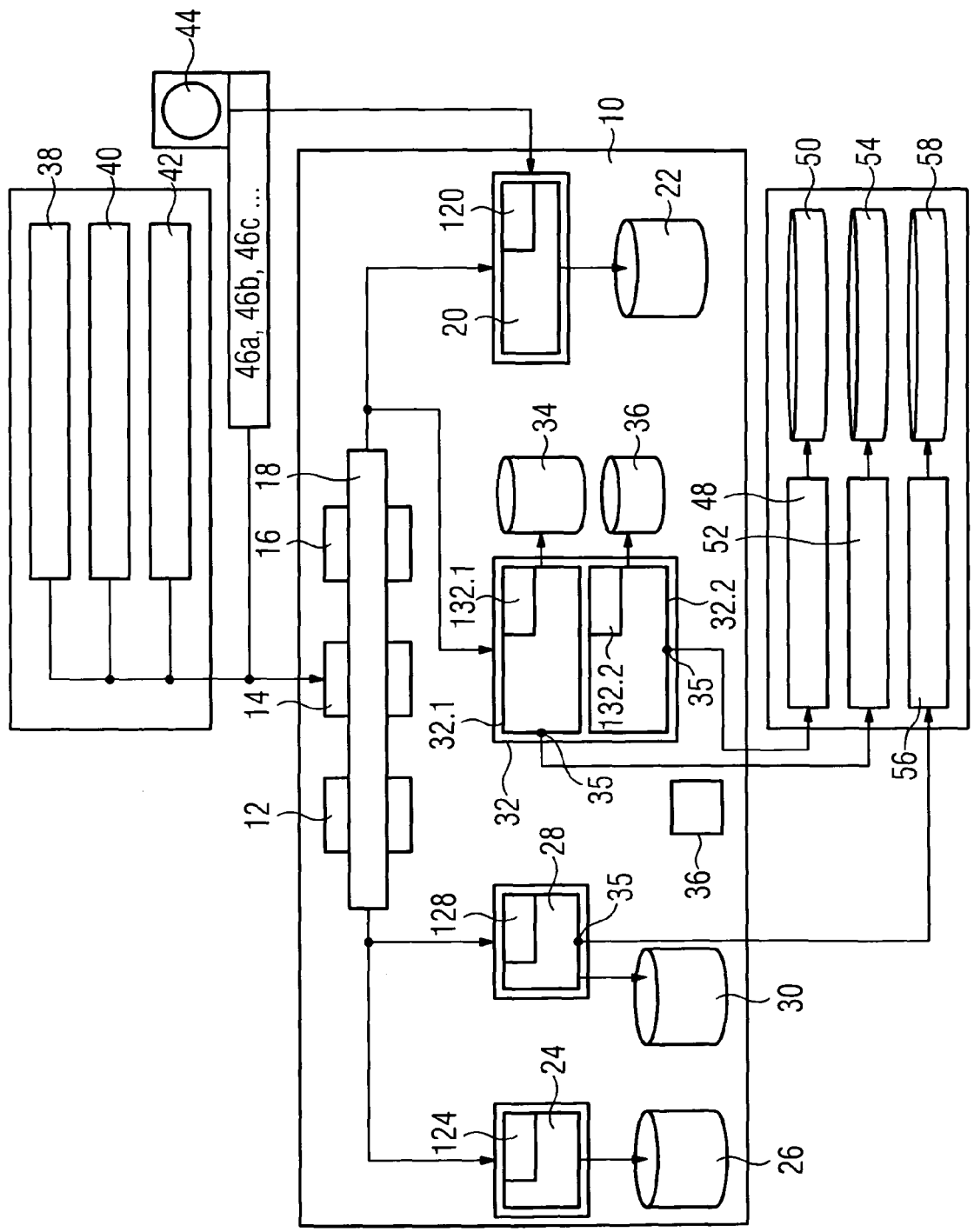

METHOD OF PROVIDING TAILOR-MADE SOFTWARE FOR HOSPITAL DEPARTMENTS

FIELD

Embodiments of the invention generally relate to a method of providing software which is tailor-made for being used in a specific department of an organization having more than one department. At least one embodiment of the invention is in particular designed for software for hospital departments.

Embodiments of the invention also generally relate to a storage medium on which program code is stored. At least one embodiment relates to software, in particular for a hospital, comprising several portions of which in different departments of a hospital some are made use of and others not.

BACKGROUND ART

A hospital may have different departments such as radiology, cardiology, and oncology. The work done by physicians and their staff in these departments differs according to the kind of department. Since software has to support that work, up to now for each kind of hospital department specific software packages are provided. They may have been provided by different provider firms such that they are possibly incompatible one with another. The manner how to use the software may differ from one department to another, for example different commands may have to be input in similar situations, therefore for staff working in different departments, the handling of the software would prove to be difficult. Moreover, the software packages for each department has to be stored for example on a particular server in the department, taking storage place which has to be obtained at high costs. The software has be installed and regularly updated, such that particular IT personnel has to be installed and regularly updated, and further such that particular IT personnel is needed for each department.

Despite different work being done by the physicians in different departments of a hospital, some departments have also in common that particular steps have to be performed. For example in many departments, if not in each department, the physician has to deal with images. These have to be stored and administrated, they have to be viewed and perhaps commented on in a particular comment file. Also, all departments of a hospital have in common that patient data have to be administrated. When providing software packages, each performing similar steps such as supporting storing and viewing of images and administrating of patient data, resources and time are wasted by not using synergies.

This is especially the case for the use of imaging systems, so-called "modalities": Similar imaging systems may be used by different departments. Imaging systems may be computer tomographs, magnetic resonance imaging systems, angiography systems, molecular imaging systems, ultrasound systems etc. A need for use of synergies may both arise, if different departments are provided with similar imaging systems each, and if different departments use a particular imaging system in common. In both cases, the software must be able to deal with the imaging systems, for example from a work station being placed in a particular department. A difficulty resides in that for each department different modalities may be used in different situations. In the radiology for example an x-ray imaging system might be in use for inspection of the bones of a patient for being able to detect fractures etc. In the cardiology, however, such x-ray system might be in use basically for viewing the heart of a patient. Therefore, the different departments cannot simply use all the same software. Particular software is needed for particular situations, which might come up in particular departments.

What has been the above for imaging systems, is also true for the administration of patient data. Here, on the one hand, it is desirable to centralize a task of administrating patient data, for example to write all information about a single patient obtained in different departments into a single file. However, different kinds of departments in hospital need different kinds of reports. The software has to support the physicians in a manner tailor-made for the particular department, when the physician is writing a report on the patient books.

SUMMARY

What is therefore needed, as recognized by the present inventors, is tailor-made software for different departments of a hospital, but in a way using synergy effects and causing less organizational and financial effort than in the prior art.

Therefore, at least one embodiment of the present invention provides software tailor-made for use in a specific department of an organization having a plurality of departments.

At least one embodiment of the invention further provides a possibility to make use of software implementing a particular task (application) and at the same time supplementing such software, in order to extend the task, wherein such extension might be made according to several possibilities, for example for different departments of a hospital a possibility each.

At least one embodiment of the present invention provides the possibility to call up computer programs, in particular tasks, by other computer programs, such that software components implementing these tasks might be organized in an optimum manner and might be supplemented in a tailor-made manner for different departments of an hospital.

At least one embodiment of the invention provides a storage medium on which program code is stored offering the possibility to provide software tailor-made for different departments of a hospital without the need for providing the entire program code to all hospital departments at the same time.

In at least one embodiment, disclosed is a method of providing software tailor-made for use in a specific department of an organization having a plurality of departments is provided, comprising the steps of providing a software package suitable for use in a plurality of departments of the organization. The software package comprises both front end and back end software components. A front end software component might be characterized in that it reacts to a user input provided via a user interface, i.e. when being run on a processor, performs at least one program step dependent on such user input. A back end software component may be characterized in that it is caused to be run to perform program steps by being called up in a program step performed by a front end software component. One back end software component may be called up by different front end software components. The method comprises the further step of adding at least one further front end software component or of adding at least one further back end software component or of adding both of such to the software package. Such added software component shall be tailor-made for use in the specific department, in particular for use together with at least one software component for the software package. This means that the further software component is not simply isolated, but cooperates with the software already provided in the basic software package.

By at least one embodiment of the present invention, it is possible to construct a software package (i.e. to program corresponding program code) allowing for the running of programs performing steps needed in at least two of the departments. Such software code does therefore not need to be programmed more than once, namely for each department. Rather, the software package can be centralized. The particular tailor-shaping of the department software is performed by providing the further software component. This further software component does not need to be able to perform all necessary steps for particular need alone. Rather, the further software component added can, when being run on a processor, cooperate with other software components being run, namely those of a centralized software package. Therefore, the further software component is a supplement to the already existing software in the software package. One might say that a further software component is complementing the software package from the viewpoint of a particular department. From the viewpoint of another department, other further software components may be provided to complement the software package. The further software components needed for one department need not be added when providing software tailor-made for another department. This means that on the servers of the departments, no program code is stored which is not needed by these departments themselves.

Not any kind of a component allows for an extension in the presently desired manner. In an example embodiment of the invention, the front end software comprises a container software component implementing a container. The definition of a container is that it is responsible for generating tasks. Tasks are generated by instantiating at least one software component, wherein the "recipe" how to build the task is read by the container from a task configuration file. In the example embodiment, a particular task configuration file structure is defined. The container is able to read any task configuration file which has been made up according to the structure and to use such task configuration file to instantiate a corresponding at least one task component, when generating a task.

The kind of container provided in the example embodiment implements a novel conception, since prior art containers are not able to read arbitrary task configuration files. Rather, prior art containers were adapted to particular tasks and were not able to generate other tasks. Having provided the container, the step of adding, in the example embodiment, comprises adding a task component for a specific task as a front end software component as well as a task component file for the specific task. The task component file shall be provided according to the particular task configuration file structure which the container of the software package is able to deal with. Providing a task configuration file according (in line) to the structure does not necessarily imply building up a task configuration file with all possible structure components. Rather, the particular task configuration file structure may be dividable into portions, for example a front end and a back end portion, and a particular task component file added might be built according to one of these portions only. The container in the software package will then be able to check portion for portion if the structure is realized in the task component file and skip those portions which are not realized.

In a further example embodiment the following features are provided which also may be provided together with a example embodiment described above. With the example embodiment described above related to the front end software components the present example embodiment relates to the back end software components. These shall comprise: At least one object component and a configuration file comprising the name of all object components, both object components and configuration file being provided for a particular task. Furthermore, the back end software components comprise a software component for instantiating configuration files, namely the configuration file mentioned above, to obtain an interface repository. An interface repository is the instantiated version of the configuration file. The instantiated version of the back end software component, i.e. a back end software component when being run on a processor, can then read information relating to the object components from the interface repository.

The conception of the use of an interface repository allows for the step of adding components providing further object components and writing the name of these further object components (and, possibly, further information) into the configuration file. It is to be noted in this example embodiment, the software package comprises software components, namely the object components, for a particular task which are supplemented by the further object components added to tailor-shape the software for a particular department. Nothing more than writing the name of a further object component into the configuration file needs to be done, and the particular task is automatically generated in an extended version, since the software component for instantiating will know from the interface repository which further object components are available.

In a further aspect of an embodiment of the present invention, a method of providing software tailor-made for a hospital department is provided, comprising the steps of providing front end and back end software. Front end software is software comprising components implementing tasks which call up components in the back end software. The method comprises adding at least one specific front end software component to extend a task in a manner tailor-made for the hospital department. In this aspect, the invention enables to provide a particular task suitable for use in more than one hospital department and to let that task run in an extended and thereby particularly adapted version. The task implemented by the non-specific components might even have an ancillary function vis-à-vis the specific component. For example, the specific component implements the task of imaging the heart of a patient and might be using general imaging tasks as a precondition but in an ancillary role.

In the further aspect of an embodiment of the invention, an example embodiment includes the step of adding at least one specific back end software component to which one specific front end software component corresponds in a manner that program code that the corresponding extended task generated by using both non-specific and the corresponding specific front end software component calls up the added specific back end software component. In the example embodiment, a software is therefore supplemented on its two levels, front end and back end, in a manner that the added software on the two levels is related, one component to the other.

In a further aspect of an embodiment of the present invention a storage medium (such as a computer readable medium for example) is provided with program code stored thereon. The program code is provided in the form of front end and back end components. At least one front end component, when run on a processor, is able to call up a back end component. Both the front end and back end component comprise general components implementing a general task for use in a hospital. For at least one general task, there are department components provided, namely for different hospital departments. These department components allow for specifically extending the corresponding general task in a tailor-made manner for each of the different hospital departments.

When having the need for software in a particular department, one can copy the general components for the general task and the department components for the particular department. Those department components for other departments are not needed. The storage medium may comprise all software needed anywhere in a hospital. However, those portions of the software have to be installed in a particular department which render the software tailor-made for this department. This means that on servers in the department, not the whole software for the hospital has to be stored. This is in line with the inventive method.

On the storage medium there may be department front end components and department back end components which are related to each other. The relationship may reside in the department front end component comprising program code which serves to call up, when the code is run on a processor, the department back end component. In other words, the extended task made up by a general front end component and the particular department front end component makes use of special software on the back end side for the same department.

BRIEF DESCRIPTION OF THE DRAWINGS

In the following an example embodiment of the invention is described with reference to the drawing, in which FIG. 1 shows a scheme of software which serves to illustrate a method according to an embodiment of the present invention.

DETAILED DESCRIPTION OF AN EXAMPLE EMBODIMENT OF THE INVENTION

An embodiment of the invention provides a conception of how software may be used in different departments of a hospital. The conception is based on using a common software package by all departments and of using supplementary software in each department. Both the software of the common software package and the supplementary software may be divided in front end and back end software.

The common software package is indicated at 10 in FIG. 1. It comprises program code packets (software components) on the front end side of the common software package 10 which implement particular applications (which correspond to tasks).

A first application 12 is a viewer application and is responsible for assisting a user placed in a department of the hospital in viewing images obtained by imaging system. Application 12 is placed in the common software package 10, because in a plurality of departments of a hospital, if not in all departments, patient images have to be viewed.

In addition to the mere viewing, the patient images have to be handled by more than one department. Therefore, the common software package 10 comprises an application 14 which is a browser application responsible for assisting a user in browsing for images in a database. The browser application 14 may call up the viewer application 12, if the user has chosen a particular image and desires to view same.

A further application in the common software package 10 is an administration application 16. This application is shared by all departments, because all departments of a hospital have to administrate patient data.

Common software package 10 further comprises a program code packet, i.e. a software component which is called a container 18. Container 18 is responsible for mapping program code from a permanent storage, such as a read only memory, to a main storage, such as a random access memory. This mapping serves to generate a particular task such as applications 12, 14, or 16. For being able to generate a task, container 18 reads a task configuration file. Presently, container 18 is able to read any task configuration file provided it is formed according to the predetermined structure. This structure is defined in the container 18 and container 18, when reading the task configuration file, looks at which content of the task configuration file corresponds to a particular structure element of the structure. For example the container firstly looks for a front end component which might be used in a task. Then, container 18 looks for a back end component which might be used in a task. In the configuration file, then, first the front end components and then the back end components have to be indicated.

Once mapped by container 18 into the main storage, in order to be run, applications 12, 14, and 16 may call up other software components, in particular software components representing particular tasks. The software components called up are back end software components. One back end software component 20 implements the task of assisting a user in acquiring images with an imaging system. This task makes use of a database 22 comprising examination protocols. These comprise information of which steps an imaging system has to perform in a particular situation, i.e. for particular needs.

A second back end software component 24 implements the task of administration indexing structures used for indexing of images and enabling a search for images. The structures make use of the DICOM Standard Structure, wherein DICOM stands for "Digital Imaging and Communications in Medicine". The indices are stored in database 26.

A further back end software component 28 implements the task of making up reports. This task makes use of a report data model stored in database 30. The report data model provides information on what a medical report has to look like. Task 28 then assists a user in preparing a report having the structure needed.

A still further back end software component 32 implements the task of managing a work flow in a hospital. It should be noted that in a hospital a patient is very often transferred from one department to another, wherein in each department a plurality of examination procedures is performed. The task represented by component 32 is therefore responsible for coordinating running applications, in particular applications running in different departments of a hospital. Component 32 is divided into two subcomponents 32.1 and 32.2.

Subcomponent 32.1 is responsible for administrating information on the patient, for example the time at which the patient is to be visited by the doctors, individual data of the patient and which orders have been attributed to the patient. This information administrated by subcomponent 32.1 is stored in database 34.

Subcomponent 32.2 is responsible for administrating task flows, wherein these task flows are stored in a database 36.

All of the back end software components implement tasks that can in principle be extended. In the present example, components 28 and subcomponents 32.1 and 32.2 have been chosen for extension. This is represented by extension points 35 schematically representing the possibility for extension.

In the present case, the software package 10 comprises a particular software component 36 (somehow corresponding to container 18 of the front end side) which is responsible for instantiating configuration files for particular software components. Configuration files for back end software components 20, 24, 28, 32 are indicated at 120, 124, 128, 132, respectively. Software component 36 therefore maps the configuration files from a permanent storage to a main storage, thereby creating what we presently call an interface repository. When the task is run, it may read out from the interface repository information regarding particular components (objects). In particular, a task can obtain information from the interface repository on the particular interface configured corresponding to an object. One component may have more than one interface, and all interfaces are indicated in the interface repository.

The software package 10 having the above-mentioned features is suited to be used by all departments of a hospital. Software package 10 can be stored on a server in each department, but may also be stored on a central server in the hospital to which workstations in all departments may have access.

In the following, it is explained how software tailor-made for a particular department may be provided. As described above, container 18 on the front end side is able to read task configuration files having a predetermined structure. Therefore, it is possible to add further tasks, thereby extending existing tasks. The tasks are added both at the front end and the back end side. Those tasks added at the front end side serve to assist a user in providing particular inputs.

Each hospital department differs in the particular task flows needed. Therefore, a front end software component 38 is added implementing the task of choosing task flows which are needed in the particular department only.

A further front end software component 40 is added implementing a task assisting a user to input, view and amend patient information specifically needed in the particular department.

Furthermore, a front end software component 42 is added implementing the task to write, view and amend medical reports which are specific for the particular department.

For each imaging system needed in the particular department and represented by a symbol indicated at 44, particular front end software components 46a, 46b, 46c are provided. These front end software components represent tasks allowing for control of the corresponding imaging system 44 according to a particular protocol. The reason for this is that a particular department needs particular information which is to be obtained by particular imaging. For example, if the particular department is the cardiology, it is needed to image the heart of a patient. The particular steps to be performed by the imaging system (modality) are provided by front end software components 46a, 46b, 46c.

Also, on the back end side, particular software is added to tailor-shape the software system as a whole for a particular department. Presently, software components may be added (so-called provider objects), and when adding such provider objects, an information on these objects is written into the configuration file of the task extended by these objects. Software components 36 will then cause information on the added provider objects to be present in the interface repository created.

One of the back end software components added is back end software component 48 extending back end software component 32.2. Whilst 32.2 is responsible for creating work flows, the extension allows for creation of work flows specific to the particular department. Database 36 is extended by provision of database 50 in which task flows specific for the particular department are stored.

Back end software component 52 is added to extend back end software component 32.1. Whilst back end software component 32.1 is responsible for administrating information needed by all departments, back end software component 52 allows for administrating information specifically needed in the particular department. In cardiology, for example, information concerning the heart of a patient is needed. Database 54 extends database 34 and comprises specific information.

A further back end software component 56 is added to extend software component 28. Whilst back end software component 28 is responsible for making up and storing reports, back end software component 56 allows for use of a report scheme specifically needed in the particular department. For example in cardiology, specific medical reports relating to the patient's heart are created. Database 58 extends database 30 and stores such specific reports.

In the following, it is exemplarily explained how tailor-made software might be used.

When a patient comes into a particular department of a hospital one usually starts with obtaining images of the patient by using a particular imaging system 44. Software component 20 assists the operator of the imaging system in performing particular steps. An operator may start by obtaining images of the kind also used in other departments and may therefore rely on back end software component 20 only. However, one of the front end software components 46a, 46b, 46c is tailor-made for using the particular imaging system 44 in the particular department. This means that the operator is enabled to obtain images specifically needed in the hospital department.

Once the images are acquired, post-processing starts. Back end software component 24 is responsible for indexing the images obtained and storing the index in database 26. Thereafter, the images can be browsed by application 14. This post-processing is not specific for the particular department.

Having viewed the images by use of application 12, the physician has made up his diagnosis. The physician has to make a medical report comprising what has been done and the diagnosis. Back end software component 28 assists the physician in this undertaking. Those components the report may have to have in the particular department are comprised under assistance of added back end software component 56.

Once the report has been made up, a department-specific information system is called up. This is provided by added back end software component 52 under assistance of back end software component 32.1. Other kinds of workflows can be run through each time at least some of the steps being supported both by software components from the software package 10 and added software components.

The software package 10 may comprise other software components than those described above which also perform other tasks. Also, additional software components can be provided in particular for additional tasks. Other software components than those described above may be added, both at the front end and the back end side. Also, some of the further software components described above may be omitted.

The common software package 10 is able to be extended. Presently on the front end, container 18 allows for extending the front end and the use of an interface repository allows for extending the back end.

Other solutions how the conception of adding tailor-made software for a hospital department to a common software package may be construed and fall under the scope of the appended claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium or storage medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

List of References
10 software package
12 front end software component
14 front end software component
16 front end software component
18 front end software component
20 back end software component
22 database
24 back end software component
26 database
28 back end software component
30 database
32 back end software component
32.1 subcomponent
32.2 subcomponent
34 database
36 Software component
38 front end software component
40 software component
42 front end software component
44 imaging system
46a front end software component
46b front end software component
46c front end software component
48 back end software component
50 Database
52 back end software component
54 Database
56 Software component
58 Database
120 configuration file
124 configuration file
128 configuration file
132.1 configuration file
132.2 configuration file

What is claimed is:

1. A method of providing software for administrating the work flow of an apparatus used in a hospital, the method comprising:
providing a software package configured for use in a plurality of departments of the hospital, the software package including at least one front end software component and at least one back end software component, the the at least one front end software component and the the at least one back end software component include code segments configured to be executed by a processor,
performing, by the processor, at least one task associated with the at least one front end software component in response to a user input provided via a user interface;
performing, by the processor, at least one task associated with the at least one back end software component in response to a call from the at least one front end software component; and
adding, by the processor, at least one further software component including at least one further front end software component and at least one further back end software component, to the provided software package, the at least one further software component being configured to implement at least one task that is specific to one of the plurality of departments of the hospital.

2. The method according to claim 1, further comprising:
defining, by the processor, a task configuration file structure, wherein
the at least one front end software component includes a container software component including code segments configured to be executed by the processor and to cause the processor to implement the container software component, the container software component being configured to generate tasks,
the container software component is configured to read any task configuration file according to the task configuration file structure and to use the task configuration file to instantiate a corresponding at least one task component during task generation, and
the at least one task that is specific to one of the departments includes a task component for a specific task of the at least one further front end software component and a task configuration file for the specific task, the task configuration file being provided according to the task configuration file structure.

3. The method according to claim 2, wherein
the at least one front end software component includes at least one task component implementing at least one general task associated with at least two of the plurality of departments, the at least one general task including at least one of,
a task of providing visible images to a user,
a task of searching the visible images, and
a task of administrating patient data, and
the task component that is for the specific task being a supplement to and suitable for being instantiated together with the at least one task component of the software package, the specific task component being configured to provide an extended version of the at least one general task, the extended version of the at least one general task being specific to one of the at least two of the plurality of departments.

4. The method of claim 1, wherein the at least one back end software component includes:

for at least one particular task, at least one object component and a configuration file including a name of all object components for the one particular task, and a software component including code segments configured to be executed by the processor and to cause the processor to instantiate the configuration file to obtain an interface repository such that the at least one back end software component reads information relating to the object components therefrom, wherein the adding at least one further software component includes providing further object components and writing the name of the further object components into the configuration file.

5. The method of claim 4, wherein the object component and the configuration file are provided for at least one general task associated with at least two of the plurality of hospital departments, a task associated with of indexing images and of storing indices in a data file, and a task associated with providing for coordination of other tasks, and the further object components are a supplement for and suitable to be instantiated together with at least one object component of the software package, thereby being configured to provide an extended version of the at least one general task, the extended version of the at least one general task being specific to one of the at least two hospital departments.

6. A method of providing software made for a hospital department from among a plurality of hospital departments, the method comprising:

providing, by a processor, at least one front end software component, the at least one front end software component including at least one task component implementing at least one general task associated with the plurality of hospital departments;

providing, by the processor, at least one back end software component such that the at least one of the back end software component includes code segments configured to be executed by the processor in response to a call from the at least one front end software component; and adding at least one further front end software component to provide an extended version of the at least one front end software component, the extend version being specific to one of the plurality of hospital departments.

7. The method of claim 6, further comprising adding at least one further back end software component, wherein, the at least one further front end software component includes program code segments such that a corresponding extended task calls the at least one back end software component.

8. A non-transitory storage medium on which program code is stored, the program code including, at least one front end component, and at least one back end component, wherein the at least one of the front end component includes code segments configured to be executed by a processor and configured to call the at least one back end component, the at least one front end component includes at least one general front end component and at least one further front end component, the at least one general front end component being configured to implement at least one general task associated with a plurality of hospital departments, and the at least one further front end component being configured to implement at least one specific task that is specific to one of the plurality of hospital departments, and the at least one back end component includes at least one general back end component and at least one further back end component, the at least one general back end component being configured to implement at least one general task associated with the plurality of hospital departments, and the at least one further back end component being configured to implement at least one specific task that is specific to one of the plurality of hospital departments, the at least one back end component being executed by the processor in response to the call.

9. The storage medium according to claim 8, wherein for at least one hospital department, the processor stores, on the storage medium, both a department-specific front end component and a department-specific back end component, and the department-specific front end component includes program code segments configured to be executed by the processor and to call the department-specific back end component.

* * * * *